United States Patent
Peeters et al.

(10) Patent No.: US 6,411,855 B1
(45) Date of Patent: Jun. 25, 2002

(54) AUDITIVE PROSTHESIS COMPRISING A CARRIER WHICH CAN BE IMPLANTED IN A COCHLEA

(75) Inventors: Stefaan E. A. Peeters, Aartselaar; Peter R. A. Deman, Desselgem, both of (BE)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 09/491,629

(22) Filed: Jan. 26, 2000

(30) Foreign Application Priority Data

Jan. 28, 1999 (EP) .............................. 99200242

(51) Int. Cl.$^7$ ................................ A61N 1/04
(52) U.S. Cl. ......................... 607/57; 607/137
(58) Field of Search .................. 607/56, 57, 58, 607/137

(56) References Cited

FOREIGN PATENT DOCUMENTS

| WO | WO 93/06698 A1 | 4/1993 | | |
|----|----------------|--------|---|---|
| WO | WO 97/26943 A1 | 7/1997 | | |
| WO | WO9738653 | 10/1997 | ........... | A61F/11/04 |
| WO | WO 97/38653 A1 | 10/1997 | | |

OTHER PUBLICATIONS

"Dimensions of the Scala Tympani in the Human and Cat with Reference to Cochlear Implants", by Shin–Ichi Hatsushika et al, Fifth International Symposium, Recent Advances in Otitis Media, May 20–23, 1991, pp. 871–872, 876.

*Primary Examiner*—Scott M. Getzow
(74) *Attorney, Agent, or Firm*—Gottlieb, Rackman & Reisman, PC

(57) ABSTRACT

An auditive prosthesis comprising an elongated carrier (31) which can be implanted in the scala tympani of a cochlea, which carrier is provided, over at least a part of its length, at a first side face with electrode elements and, at a second side face (32b) facing away from the first side face (32a), with an electric conductor. Said side faces are interconnected by a third side face (32c) and a fourth side face (32d), said first side face extending, in a state where the carrier is implanted in the scala tympani, opposite the basilar membrane of the cochlea. In order to achieve, after implantation, an information transfer to the auditory nerve which is as complete as possible, the third side face and the fourth side face of the carrier are arranged, over at least a part of the length of the carrier where electrode elements are present, at distances from each other which are at least substantially equal to corresponding dimensions of the scala tympani which are parallel to the basilar membrane. After implantation of the carrier, the scala tympani is at least substantially completely filled, over at least a part of the area extending between the fenestra cochlea and the helicotrema, in a zone extending parallel to the basilar membrane.

32 Claims, 3 Drawing Sheets

AUDITIVE PROSTHESIS COMPRISING A CARRIER WHICH CAN BE IMPLANTED IN A COCHLEA

BACKGROUND OF THE INVENTION

The invention relates to an auditive prosthesis comprising an elongated carrier which can be implanted in the scala tympani of a cochlea, which carrier is provided, over at least a part of its length, with electrode elements at a first side face and, at a second side face facing away from the first side face, with an electric conductor, which side faces are interconnected by a third side face and a fourth side face, the first side face extending, in a state in which the carrier is implanted in the scala tympani, opposite the basilar membrane of the cochlea.

Such an auditive prosthesis is known from WO 97/38653 (PHQ 96.025). The known prosthesis comprises a silicone carrier provided with a set of electrodes, which silicone carrier can be operatively implanted in a scala tympani of a cochlea to improve the hearing capacity of a hearing-impaired person. Said set includes a series of electrode contacts arranged on a side of the carrier and a central electrode arranged on an opposite side. After implantation of the carrier, electric currents can be sent through the electrodes, in dependence upon received sound signals, to stimulate nerve fibers of the auditory nerve present in the modiolis so as to induce electrical signals into the auditory nerve. Via nerve fibers, these signals are guided to the brain to interpret sound signals.

Said known prosthesis is provided with a swelling member which is provided on a side face interconnecting the two above-mentioned sides, which swelling member, after implantation of the carrier, serves to urge the carrier against the modiolis. Although a reasonable stimulation of the auditory nerve can be achieved in this way, relatively many electric currents between the electrode contacts and the central electrode still run via the perilymph, so that considerable parts of the electric currents supplied for stimulation are lost and hence only a limited information transfer to the neural system in the modiolis takes place.

It is an object of the invention to improve the auditive prosthesis mentioned in the opening paragraph in such a manner that, after implantation, said prosthesis can highly efficiently transfer information to the auditory nerve.

SUMMARY OF THE INVENTION

To achieve this, the auditive prosthesis in accordance with the invention is characterized in that, over at least a part of the length of the carrier where electrode elements are present, the third side face and the fourth side face of the carrier are situated at distances from each other which are at least substantially equal to corresponding dimensions of the scala tympani which extend parallel to the basilar membrane, in order to at least substantially completely fill the scala tympani, after implantation, over at least a part of the area extending between the fenestra cochlea (round window) and the helicotrema in a zone extending parallel to the basilar membrane.

The auditive prosthesis in accordance with the invention is intended to bring about a sound perception in patients who are hard of hearing, very hard of hearing or deaf, which sound perception may give rise to the hearing of speech by means of an efficient electrical stimulation of the auditory nerve.

The above-mentioned carrier with electrode elements forms an internally implantable part of the auditive prosthesis in accordance with the invention. The auditive prosthesis may additionally comprise an externally implantable part, which is provided with means for receiving sound signals and with a speech processor for converting these signals to electrical signals. By means of algorithms, the sound caught can be processed to imitate the operation of a normal inner ear. Such a processing step may result in coded information which can be passed on to the internal part where this information is converted to electric currents between the electrode elements and the conductor present. The number of individually drivable electrode elements may range, for example between 28 and 35, although other numbers are possible too.

By means of the measure used in the auditive prosthesis it has been achieved that, after a correctly performed implantation, the first side face of the carrier faces the basilar membrane, the electrode elements being very close to the habenula perforations. The habenula perforations are openings in the bone structure bordering on the scala tympani, which openings guide the dendrites of the afferent nerve fibers of the internal hair cells along the ganglion cells to the higher auditive centers in the brain. The applied measure leads to a well-definable interface between the carrier and the neural system, which can be attributed to the fact that the space of the scala tympani can be filled in such a way by a correctly implanted carrier that in the zone extending parallel to the basilar membrane there is no, or hardly any perilymph between the carrier and the partition of the scala tympani, so that the resistance path between the electrode elements at the first side face and the conductor at the second side face is maximal. Consequently, the currents generated for stimulation are more efficiently used to stimulate the nerve fiber structure in the modiolis.

An embodiment of the auditive prosthesis in accordance with the invention is characterized in that, over at least the part of the carrier where electrode elements are present, the first side face and the second side face of the carrier are at distances from each other which are at least substantially equal to corresponding dimensions of the scala tympani which extend transversely to the basilar membrane, in order to at least substantially completely fill the scala tympani, after implantation, over at least a part of the area extending between the fenestra cochlea and the helicotrema in a zone extending transversely to the basilar membrane.

By means of the measure applied in this embodiment it is achieved, after a correct implantation of the carrier in the scala tympani, that the first face of the carrier, which is provided with electrode elements, lies against the basilar membrane and the adjoining part of the modiolis, in particular the laminae spiralis osseae, which has a favorable effect on the transfer of electric currents from the electrode elements to the habenula perforations. Besides, electrode elements situated as closely to the nerve fibers as possible counteract disturbing channel interactions.

An embodiment of the auditive prosthesis in accordance with the invention is characterized as defined in claim 3.

An embodiment of the auditive prosthesis in accordance with the invention is characterized as defined in claim 4.

In the practical embodiments in accordance with claims 3 and 4, the carrier is optimally adapted to the anatomy of the cochlea of human beings.

In an embodiment of the auditive prosthesis in accordance with the invention the first side face of the carrier is an at least substantially flat or, possibly, slightly curved surface, the electrode elements being provided with flat contact faces which are situated in or below the above-mentioned surface.

Consequently, the first side face does not have projecting parts, so that said face accurately corresponds to the shape of the inner side of the scala tympani which is situated near the basilar membrane and the adjoining part of the modiolis, which, on the one hand, is important to preclude damage to the basilar membrane during the provision of the carrier and, on the other hand, has a favorable effect on the information transfer, after the provision of the carrier. If the contact faces do not extend in the surface of the carrier, they are preferably situated directly underneath said surface. This is the case, for example, if the electrode elements are retained in the carrier by means of an overhanging edge of carrier material.

It is noted that the application of the measure in accordance with claim 1, whether or not in combination with the measure in accordance with claim 2, leads to a carrier which is relatively voluminous of itself and hence to an auditive prosthesis of which at least two side faces, even four side faces if the measure in accordance with claim 2 is applied, may closely contact the partitions of the scala tympani during inserting the carrier into the scala tympani. It has nevertheless been found that this does not have any adverse effects for the patient if the implantation is carried out correctly and if a flat first side face is used. In addition, it has surprisingly been found that the prosthesis with a flat first side face can be removed from the cochlea without damaging the scala tympani, more specifically the basilar membrane.

An embodiment of the auditive prosthesis is characterized in that the contact faces of the electrode elements are arranged according to a series extending in the longitudinal direction of the carrier, at least a number of the contact faces present being oval faces whose longitudinal axes are oriented transversely to the longitudinal direction of the carrier. An advantage of this embodiment resides in that, in spite of a high density of electrode elements, the carrier has a relatively high flexibility, which is favorable during inserting the carrier into the spiral-shaped scala tympani. The applied measure also enables the use of relatively large contact faces, which has a favorable effect on the impedance between the contact faces and the perilymph. In addition, the use of larger contact faces enables a smaller current density to be used, which is important in precluding undesirable electrochemical reactions at the location of the contact faces.

An embodiment of the auditive prosthesis in accordance with the invention is characterized in that the contact faces of the electrode elements have a rough surface. Contact faces having a certain degree of roughness have a larger effective contact surface area and hence a lower impedance than smooth contact faces. Preferably, the contact faces of the auditive prosthesis are provided with a coating, in particular an impedance-reducing coating, such as iridium oxide, in which case the roughness also has a favorable effect on the adhesion of the coating. The electrode elements themselves are preferably made of an inert material, such as platinum.

The invention further relates to a carrier which can suitably be used in the auditive prosthesis in accordance with the invention. The carrier in accordance with the invention is characterized as described in any one of the claims 1 through 7.

The invention further relates to an elongated, preferably pre-bent, carrier which is provided over at least a part of its length, at a first side face, with electrode elements and which can be implanted in one of the tubular spaces, such as the scala tympani, the scala vestibuli or the scala media, of a cochlea. In order to enable the side face provided with electrode elements to connect closely, after the implantation of the carrier, to a corresponding wall part of the cochlea, the carrier in accordance with the invention is characterized in that the first side face is an at least substantially flat or, possibly, slightly curved surface, the electrode elements being provided with flat contact faces situated in or below said surface. Consequently, in said first side face there are no projecting parts, thereby counteracting damage of the cochlea during implantation, and enabling, after implantation, said side face to be in close contact with an inner wall of the cochlea. The carrier in accordance with the invention thereby achieves the object that it should be possible, after implantation, to highly efficiently transfer information to the auditory nerve.

Preferably, the contact faces of the electrode elements are arranged in accordance with a series extending in the longitudinal direction of the carrier, at least a number of the contact faces present being oval or oval-like faces having axes which are oriented transversely to the longitudinal direction of the carrier. The carrier will generally be provided at a second side face with one or more electric conductors to form a suitable electric circuit.

In an embodiment of the carrier in accordance with the invention, the contact faces of the electrode elements have a rough surface.

With respect to the claims it is noted that various combinations of characteristics defined in the claims are possible.

These and other aspects of the invention will be apparent from and elucidated with reference to the embodiment(s) described hereinafter.

DETAILED DESCRIPTION OF THE INVENTION

Figure 1:
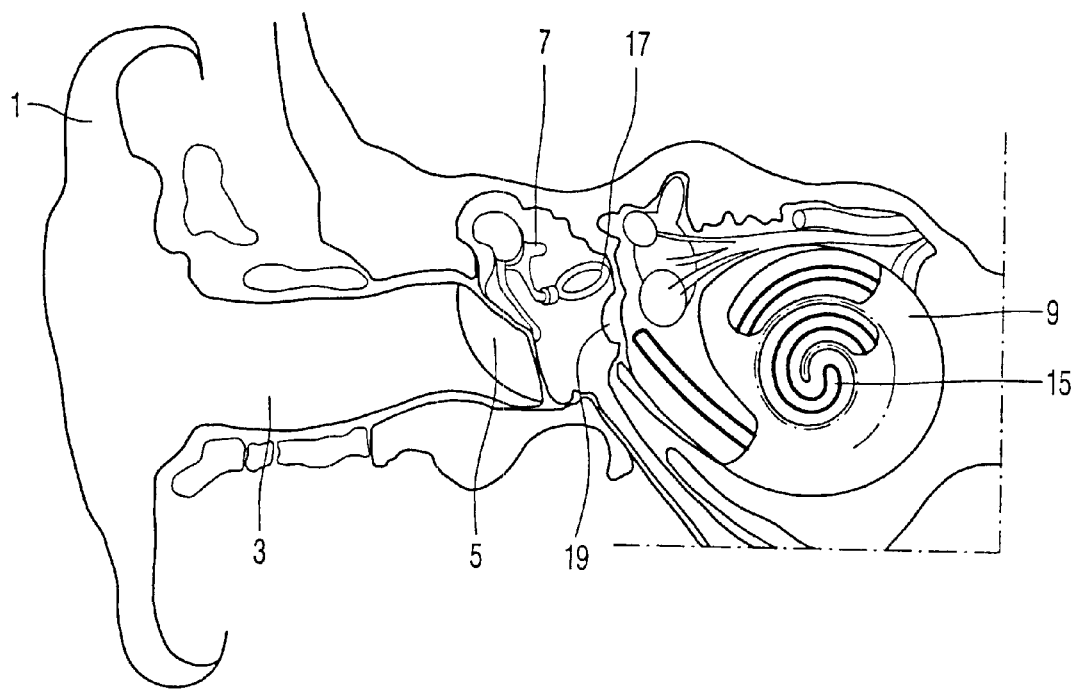
FIG. 1 diagrammatically shows the anatomy of a human ear.
Figure 2:
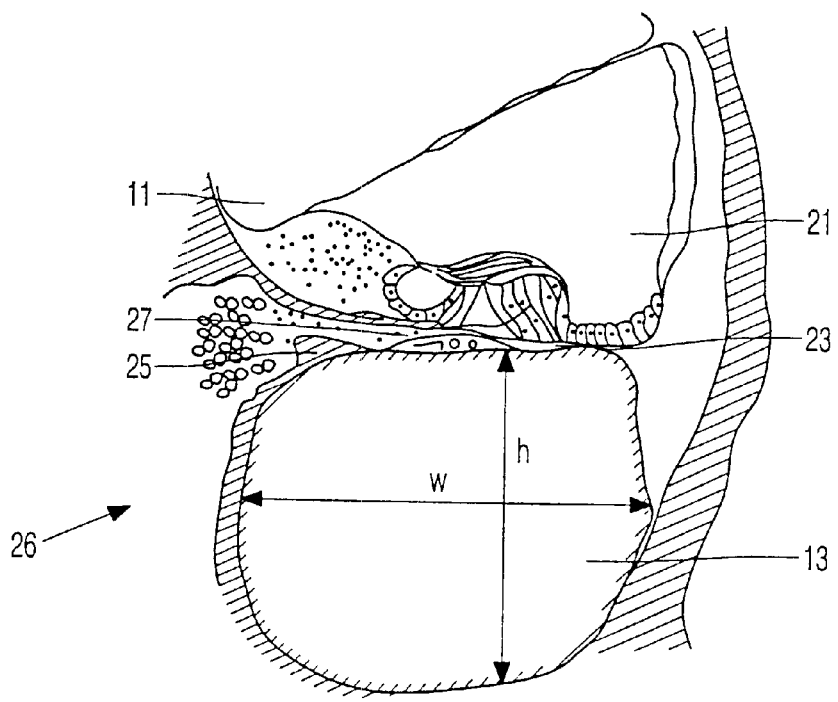
FIG. 2 is a diagrammatic, cross-sectional view of the scala tympani of the cochlea of the human ear (the drawing is taken from Hatsushika et al., Dimensions of Scala Tympani, pp. 872, 876; Fifth International Symposium on Recent Advance in Otitis Media; May 20–23, 1991)

The human ear diagrammatically shown in FIGS. 1 and 2 comprises an outer ear with an auricle 1 and an auditory duct 3, a middle ear which borders on the outer ear by means of an eardrum 5 and which is provided with ossicles 7, and an inner ear with a cochlea 9. Said cochlea 9 is situated in the petrosal bone and is provided with a spiral-shaped network comprising the scala vestibuli 11 and the scala tympani 13, which are interconnected in the apex of the cochlea via the helicotrema 15. At the base of the cochlea 9 there are two windows, one of which, i.e. the oval window 17 in which one of the ossicles 7 fits, closes the scala vestibuli 11, and the other, i.e. the round window 19, which connects to the middle ear cavity, closes the scala tympani 13. Between these scalae, there is the scala media 21 with a sensorial organ, referred to as Corti's organ. The scala tympani 13 is filled with perilymph, which is a fluid whose ion composition resembles that of extracellular fluid. Between the scala media 21 and the scala tympani 13 extends the basilar membrane 23. The lamina spiralis osseae 25 of the modiolis 26 and the habenula perforations 27 are situated between the scala vestibuli 11 and the scala tympani.

Figure 3:
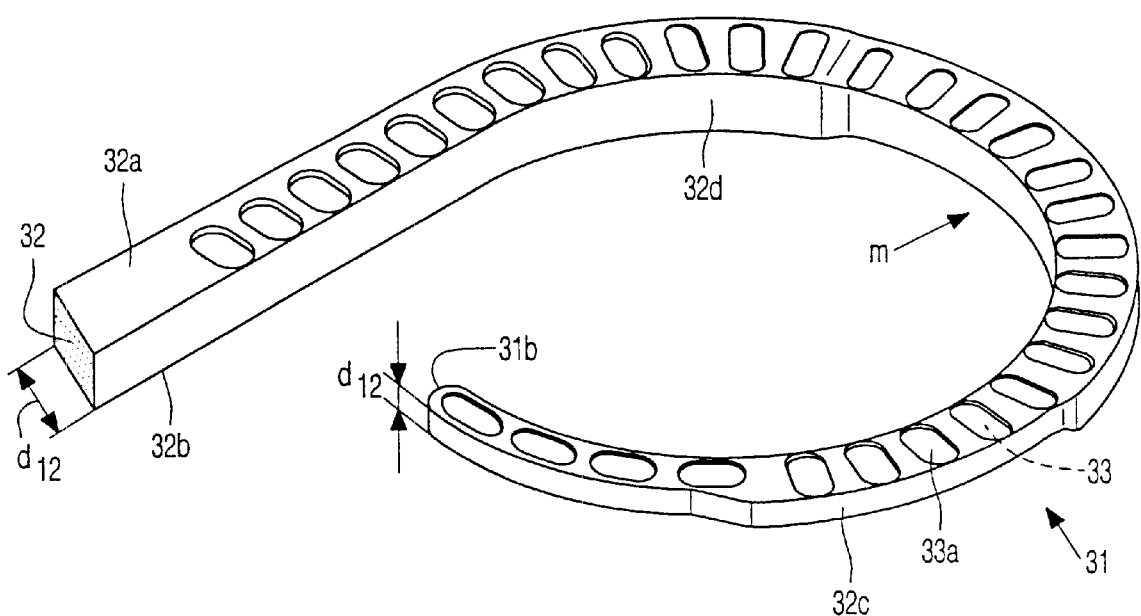
FIG. 3 is a perspective view of a part of an embodiment of the carrier in accordance with the invention.
Figure 6:
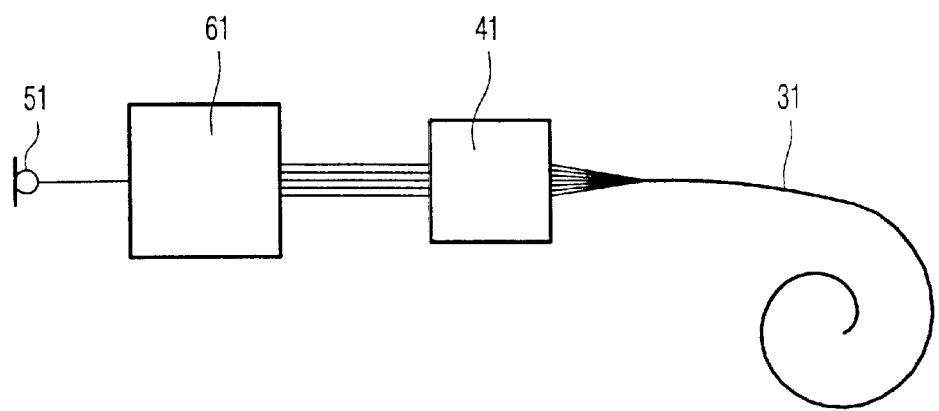
Figure 4:
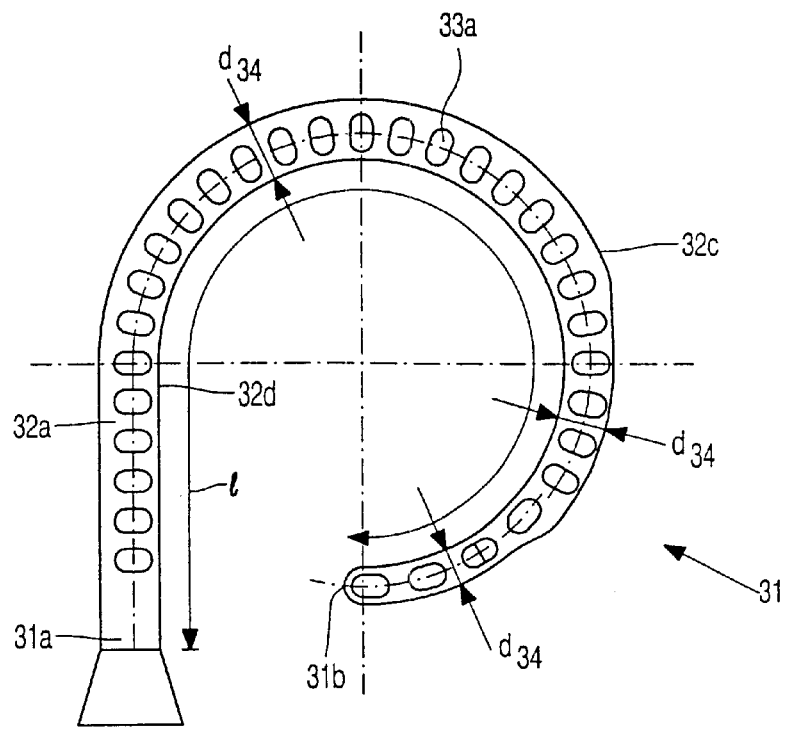
FIG. 4 is a diagrammatic plan view of the embodiment shown in FIG. 3.
Figure 5:
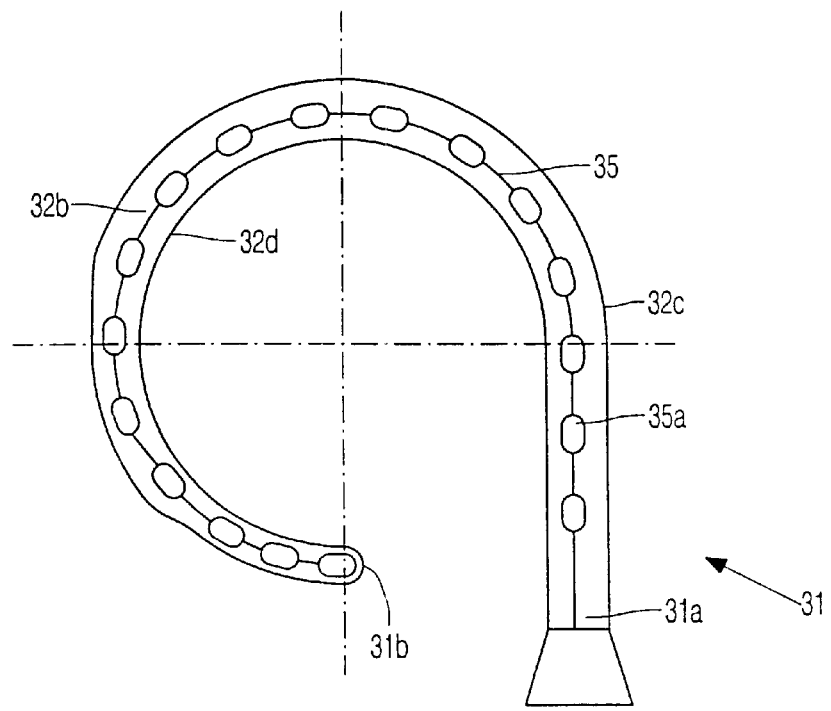
FIG. 5 is a diagrammatic bottom view of the embodiment shown in FIG. 3, and FIG. 6 diagrammatically shows an embodiment of the auditive prosthesis in accordance with the invention.

The elongated pre-bent carrier 31, which is shown in FIGS. 3, 4 and 5 and which includes electrode elements 33 is to be implanted in a cochlea, in particular in the scala tympani thereof. For clarity reference will be made, if necessary, to the cochlea 9 shown in FIGS. 1 and 2. The carrier 31, which has a length 1 between its base 31a and its top 31b, is provided, in this example, with a carrier body 32 of silicones in which the electrode elements 33 as well as an electric conductor 35, which is embodied so as to be a longitudinal electrode, are provided. In this example, the length 1 is 29 mm. The electrode elements 33, which are provided with flat contact faces 33a, are situated at a first side face 32a of the carrier 31, while the electric conductor 35, which extends at least substantially throughout the length of the carrier 31, is situated at a second side face 32b facing away from the first side face 32a. For securing the electric conductor 35 and for giving the carrier 31 sufficient flexibility, the electric conductor 35 comprises, in this example, a number of electrical electrode faces 35a, which are arranged in series and which are preferably situated in or below the surface formed by the second side face 32b. The number of electrode faces amounts to 17. Said side faces 32a and 32b are interconnected by two further side faces, i.e. a third side face 32c and a fourth side face 32d.

The shape and dimensions of the carrier 31 in accordance with the invention are such that, after a correct implantation of the carrier 31 in the scala tympani 13, the first side face 32a extends opposite the basilar membrane 23 and constitutes a perfect interface with the neural system. For this purpose, the third side face 32c and the fourth side face 32d, viewed over at least a substantial part of the length 1 of the carrier 31, are at mutual distances $d_{34}$, which are equal, or substantially equal, to the corresponding internal maximum width dimensions w of the scala tympani 13 which are oriented parallel to the basilar membrane 23. To this end, the first side face 32a and the second side face 32b, viewed over at least a substantial part of the length 1 of the carrier 31, are additionally situated at mutual distances $d_{12}$ which are equal, or substantially equal, to the corresponding internal maximum height dimensions h for the scala tympani 13 which extend transversely to the basilar membrane. In addition, the first side face 32a of the support 31 is embodied so as to be a flat surface, which is to be taken to mean a surface without projecting parts or elements.

Hereinafter a further description of the carrier 31 will be given, with reference to the FIGS. 3, 4 and 5. As will be obvious from the foregoing description. the carrier 31 has local transverse dimensions $d_{34}$ over a part of its length 1, which correspond to corresponding local width dimensions w of the scala tympani 13, and local height dimensions $d_{12}$ which correspond to corresponding local height dimensions h of the scala tympani 13. In this example, the carrier 31 has thirty one contact faces 32a. In the area indicated by m, i.e. the area measured along the longitudinal axis of the carrier 31, which is situated approximately centrally between the two outermost contact faces 32a, the dimension $di_2$ is 800 $\mu$m and the dimension $d_{34}$ is 1000 $\mu$m, in this example. Towards the base 31a. the dimensions $d_{12}$ and d, increase gradually or stepwise to respectively 1000 $\mu$m and 1200 $\mu$m. Towards the top 31b the dimensions $d_{12}$ and $d_{34}$, decrease gradually or stepwise to respectively 600 $\mu$m and 750 $\mu$m. As seen in the Figures, for example in FIG. 3, and as described above, carrier 31 has a substantially rectangular cross-section and is dimensioned so that at least equal to the corresponding dimensions of the scala tympani so that the carrier substantially completely fills the scala tympany after implantation, over at least a part of the area extending between the fenestra cochlea and the helicotrema.

In the present example, the theoretically flat contact faces 33a are situated slightly below the theoretically flat surface of the first side face 32a. The electrode elements 33, as well as the associated contact faces 33a, are arranged in accordance with a series extending in the longitudinal direction of the carrier 31, the contact faces 33a being embodied so as to be oval faces. With the exception of several contact faces situated near the top 31b, the contact faces have longitudinal axes $1_c$ which are oriented transversely to the longitudinal direction of the carrier 31. In this example, these faces are essentially rectangular, yet provided with round end portions. In this example, the electrode elements are made of platinum, and a thin coating of iridium oxide is applied to the slightly rough contact surfaces. The electrode elements each have a surface area of approximately 0.4 mm².

It is noted that the invention is not limited to the examples shown herein. For example, carriers having a side face provided with a different number of contact faces fall within the scope of the invention. In addition, instead of flat side faces, one or more slightly curved side faces may be used. In general, the dimension $d_{12}$ ranges between 700 $\mu$m and 900 $\mu$m, the second side face 32b and the first side face 32a enclosing an average slope angle in the range between 0.5° and 1.5°. The dimension $d_{34}$ generally ranges between 900 $\mu$m and 1100 $\mu$m, the side faces 32c and 32d enclosing an average slope angle in the range between 0.5° and 1.5°.

What is claimed is:

1. An auditive prosthesis comprising an elongated carrier which can be implanted in the scala tympani of a cochlea, which carrier is provided, over at least a part of its length, with electrode elements at a first side face and, at a second side face facing away from the first side face, with an electric conductor, which side faces are interconnected by a third side face and a fourth side face, the first side face extending, in a state in which the carrier is implanted in the scala tympani, opposite the basilar membrane of the cochlea, characterized in that, over at least a part of the length of the carrier where electrode elements are present, the third side face and the fourth side face of the carrier are situated at distances from each other which are at least substantially equal to corresponding dimensions of the scala tympani which extend parallel to the basilar membrane, in order to at least substantially completely fill the scala tympani, after implantation, over at least a part of the area extending between the fenestra cochlea and the helicotrema in a zone extending parallel to the basilar membrane.

2. An auditive prosthesis as claimed in claim 1, characterized in that, over at least the part of the carrier where electrode elements are present, the first side face and the second side face of the carrier are at distances from each other which are at least substantially equal to corresponding dimensions of the scala tympani which extend transversely to the basilar membrane, in order to at least substantially completely fill the scala tympani, after implantation, over at least a part of the area extending between the fenestra cochlea and the helicotrema in a zone extending transversely to the basilar membrane.

3. An auditive prosthesis as claimed in claim 1, characterized in that the carrier has a base and a top, the distances between the third side face and the fourth side face decreasing in the direction of said top, the third side face and the fourth side face extending at a mutual distance between 900 μm and 1100 μm in a central area of the part where electrode elements are present, and the third side face and the fourth side face enclosing an average slope angle ranging between 0.5° and 1.5°.

4. An auditive prosthesis as claimed in claim 2, characterized in that the carrier has a base and a top, the distances between the first side face and the second side face decreasing in the direction of said top, the first side face and the second side face extending at a mutual distance ranging between 700 μm and 900 μm in a central area of the part where electrode elements are present, and the first side face and the second side face enclosing an average slope angle ranging between 0.5° and 1.5°.

5. An auditive prosthesis as claimed in claim 1, characterized in that the first side face of the carrier forms a surface, the electrode elements being provided with flat contact faces which are situated in or below the above-mentioned surface.

6. An auditive prosthesis as claimed in claim 5, characterized in that the contact faces of the electrode elements are arranged according to a series extending in the longitudinal direction of the carrier, at least a number of the contact faces present being oval faces, whose longitudinal axes are oriented transversely to the longitudinal direction of the carrier.

7. An auditive prosthesis as claimed in claim 5, characterized in that the contact faces of the electrode elements have a rough surface.

8. An auditive prosthesis as claimed in claim 1, further comprising a microphone and a speech processor.

9. A carrier adapted for use in an auditive prosthesis and that can be implanted in the scala tympani of a cochlea, which carrier comprises a body having a first, second, third and fourth side face and which is provided over at least a part of its length, with electrode elements at said first side face and, at said second side face facing away from the first side face, with an electric conductor, the first side face extending, in a state in which the carrier is implanted in the scala tympani, opposite the basilar membrane of the cochlea, wherein over at least a part of the length of the carrier where electrode elements are present, the third side face and the fourth side face of the carrier are situated at distances from each other which are at least substantially equal to corresponding dimensions of the scala tympani which extend parallel to the basilar membrane, in order to at least substantially completely fill the scala tympani, after implantation, over at least a part of the area extending between the fenestra cochlea and the helicotrema in a zone extending parallel to the basilar membrane.

10. A carrier which can suitably be implanted in a cochlea, which carrier comprises a body that is elongated, has a substantially rectangular cross section and is provided, over at least a part of its length, at a first side face, with electrode elements, wherein the first side face forms a surface, the electrode elements being provided with flat contact faces which are situated in or below said surface.

11. A carrier as claimed in claim 10, characterized in that the contact faces of the electrode elements are arranged in accordance with a series extending in the longitudinal direction of the carrier, at least a number of the contact faces present being oval faces whose longitudinal axes are oriented transversely to the longitudinal direction of the carrier.

12. A carrier as claimed in claim 11, characterized in that the contact faces of the electrode elements have a rough surface.

13. A carrier as claimed in claim 10, characterized in that the carrier is provided, at a second side face facing away from the first side face, with an electric conductor which comprises electrode faces, which are situated in or below a surface formed by the second side face.

14. An auditive prosthesis comprising an elongated carrier which can be implanted in the scala tympani of a cochlea, which carrier is provided with an elongated, substantially rectangular body with a first side face, a second side face facing away from said first and second side faces, and third and fourth side faces, said third and fourth side faces being opposed to each and connecting said first and second side faces;

said carrier having over at least a part of its length electrode elements at said first side face and said second side face;

the first side face extending, in a state in which the carrier is implanted in the scala tympani, opposite the basilar membrane of the cochlea;

wherein, over at least a part of the length of the carrier where electrode elements are present, the third side face and the fourth side face of the carrier are situated at distances from each other which are at least substantially equal to corresponding dimensions of the scala tympani which extend parallel to the basilar membrane, in order to at least substantially completely fill the scala tympani, after implantation, over at least a part of the area extending between the fenestra cochlea and the helicotrema in a zone extending parallel to the basilar membrane.

15. An auditive prosthesis as claimed in claim 14, characterized in that the carrier has a base and a top, the distances between the third side face and the fourth side face decreasing in the direction of said top, the third side face and the fourth side face extending at a mutual distance between 900 μm and 1100 μm in a central area of the part where electrode elements are present, and the third side face and the fourth side face enclosing an average slope angle ranging between 0.5° and 1.5°.

16. An auditive prosthesis as claimed in claim 14, characterized in that, over at least the part of the carrier where electrode elements are present, the first side face and the second side face of the carrier are at distances from each other which are at least substantially equal to corresponding dimensions of the scala tympani which extend transversely to the basilar membrane, in order to at least substantially completely fill the scala tympani, after implantation, over at least a part of the area extending between the fenestra cochlea and the helicotrema in a zone extending transversely to the basilar membrane.

17. An auditive prosthesis as claimed in claim 16, characterized in, that the carrier has a base and a top, the distances between the first side face and the second side face decreasing in the direction of said top, the first, side face and the second side face extending at a mutual distance ranging between 700 μm and 900 μm in a central area of the part where 5 electrode elements are present, and the first side face and the second side face enclosing an average slope angle ranging between 0.5° and 1.5°.

18. An auditive prosthesis as claimed in claim 14, characterized in that the first side face of the carrier forms a surface, the electrode elements being provided with flat contact faces which are situated in or below the above-mentioned surface.

19. An auditive prosthesis as claimed in claim 18, characterized in that the contact faces of the electrode elements are arranged according to a series extending in the longitudinal direction of the carrier, at least a number of the contact faces present being oval faces, whose longitudinal axes are oriented transversely to the longitudinal direction of the carrier.

20. An auditive prosthesis as claimed in claim 18, characterized in that the contact faces of the electrode elements have a rough surface.

21. An auditive prosthesis as claimed in claim 14 further comprising a microphone and a speech processor.

22. An auditive prosthesis comprising an elongated carrier which can be implanted in the scala tympani of a cochlea, which carrier is provided with an elongated, substantially rectangular body with a first side face, a second side face facing away from said first and second side faces, and third and fourth side faces, said third and fourth side faces being opposed to each and connecting said first and second side faces;

said carrier having over at least a part of its length a first set of electrode elements at said first side face and a second electrode on another of said faces;

wherein the first side face extending, in a state in which the carrier is implanted in the scala tympani, opposite the basilar membrane of the cochlea;

and wherein, over at least a part of the length of the carrier where electrode elements are present, the body has dimensions that at least substantially equal to corresponding dimensions of the scala tympani which extend parallel to the basilar membrane, in order to at least substantially completely fill the scala tympani, after implantation, over at least a part of the area extending between the fenestra cochlea and the helicotrema in a zone extending parallel to the basilar membrane.

23. An auditive prosthesis as claimed in claim 22, characterized in that the carrier has a base and a top, the distances between the third side face and the fourth side face decreasing in the direction of said top, the third side face and the fourth side face extending at a mutual distance between 900 $\mu$m and 1100 $\mu$m in a central area of the part where electrode elements are present, and the third side face and the fourth side face enclosing an average slope angle ranging between 0.5° and 1.5°.

24. An auditive prosthesis as claimed in claim 22, characterized in that, over at least the part of the carrier where electrode elements are present, the first side face and the second side face of the carrier are at distances from each other which are at least substantially equal to corresponding dimensions of the scala tympani which extend transversely to the basilar membrane, in order to at least substantially completely fill the scala tympani, after implantation, over at least a part of the area extending between the fenestra cochlea and the helicotrema in a zone extending transversely to the basilar membrane.

25. An auditive prosthesis as claimed in claim 24, characterized in that the carrier has a base and a top, the distances between the first side face and the second side face decreasing in the direction of said top, the first, side face and the second side face extending at a mutual distance ranging between 700 $\mu$m and 900 $\mu$m in a central area of the part where 5 electrode elements are present, and the first side face and the second side face enclosing an average slope angle ranging between 0.5° and 1.5°.

26. An auditive prosthesis as claimed in claim 22, characterized in that the first side face of the carrier forms a surface, the electrode elements being provided with flat contact faces which are situated in or below the above-mentioned surface.

27. An auditive prosthesis as claimed in claim 26, characterized in that the contact faces of the electrode elements are arranged according to a series extending in the longitudinal direction of the carrier, at least a number of the contact faces present being oval faces, whose longitudinal axes are oriented transversely to the longitudinal direction of the carrier.

28. An auditive prosthesis as claimed in claim 18, characterized in that the contact faces of the electrode elements have a rough surface.

29. An auditive prosthesis as claimed in claim 28 further comprising a microphone and a speech processor.

30. An auditive prosthesis as claimed in claim 22 wherein said second electrode is on said second side face.

31. An auditive prosthesis comprising an elongated carrier which can be implanted in the scala tympani of a cochlea, which carrier is provided, over at least a part of its length, with electrode elements at a first side face and, at a second side face facing away from the first side face, with an electric conductor, which side faces are interconnected by a third side face and a fourth side face, the first side face extending, in a state in which the carrier is implanted in the scala tympani, opposite the basilar membrane of the cochlea, wherein, over at least a part of the length of the carrier where electrode elements are present, the third side face and the fourth side face of the carrier are situated at distances from each other which are at least substantially equal to corresponding dimensions of the scala tympani which extend parallel to the basilar membrane, in order to at least substantially completely fill the scala tympani, after implantation, over at least a part of the area extending between the fenestra cochlea and the helicotrema in a zone extending parallel to the basilar membrane;

wherein said carrier has a base and a top, the distances between the third side face and the fourth side face decreasing in the direction of said top, the third side face and the fourth side face extending at a mutual distance between 900 $\mu$m and 1100 $\mu$m in a central area of the part where electrode elements are present, and the third side face and the fourth side face enclosing an average slope angle ranging between 0.5 and 1.5°.

32. An auditive prosthesis comprising an elongated carrier which can be implanted in the scala tympani of a cochlea, which carrier is provided, over at least a part of its length, with electrode elements at a first side face and, at a second side face facing away from the first side face, with an electric conductor, which side faces are interconnected by a third side face and a fourth side face, the first side face extending, in a state in which the carrier is implanted in the scala tympani, opposite the basilar membrane of the cochlea, wherein, prior to implantation, over at least a part of the length of the carrier where electrode elements are present, the third side face and the fourth side face of the carrier are situated at distances from each other which are at least substantially equal to corresponding dimensions of the scala tympani which extend parallel to the basilar membrane, in order to at least substantially completely fill the scala tympani, after implantation, over at least a part of the area extending between the fenestra cochlea and the helicotrema in a zone extending parallel to the basilar membrane.

* * * * *